(12) United States Patent
da Silva Correia

(10) Patent No.: US 8,480,764 B1
(45) Date of Patent: Jul. 9, 2013

(54) PROCESS FOR CONVERTING CELLULOSE INTO A LIQUID BIOFUEL USING AS AN INTERMEDIATE AN ACETAL OF HYDROXYMETHYL FURFURAL

(75) Inventor: Pedro Manuel Brito da Silva Correia, Estoril (PT)

(73) Assignee: Pedro Correia, Estoril (PT)

( * ) Notice: Subject to any disclaimer, the term of this patent is extended or adjusted under 35 U.S.C. 154(b) by 8 days.

(21) Appl. No.: 13/371,410

(22) Filed: Feb. 11, 2012

(51) Int. Cl.
*C10L 1/18* (2006.01)
*C07D 307/36* (2006.01)

(52) U.S. Cl.
USPC .......................................... 44/352; 549/506

(58) Field of Classification Search
USPC ............................................ 44/352; 549/506
See application file for complete search history.

(56) References Cited

U.S. PATENT DOCUMENTS 8,324,409 B2 * 12/2012 Rauchfuss et al. ............ 549/506

* cited by examiner

*Primary Examiner* — Bernard Dentz

(57) ABSTRACT

Process for converting cellulose and hemicellulose into dimethyl furan, hydrolysing first cellulose in a mixture of N alkyl imidazolium chloride, hydrochloric acid 37% and an alcohol, to produce an acetal of glucose, making the dehydration to an acetal of hydroxymethyl furfural, extracting and making the hydrogenation of this acetal and distilling to produce dimethyl furan.

8 Claims, No Drawings

PROCESS FOR CONVERTING CELLULOSE INTO A LIQUID BIOFUEL USING AS AN INTERMEDIATE AN ACETAL OF HYDROXYMETHYL FURFURAL

1. FIELD OF INVENTION

Liquid biofuels from cellulose, ionic liquids, renewable energy, solvent extraction from ionic liquids

2. BACKGROUND OF THE INVENTION The world production of cellulose on land is 40 billion ton per year and the stock of cellulose is 700 billion ton.

The world consumption of fossil fuels is 8 billion ton per year.

The food production in the world is 3 billion ton per year.

From these 3 numbers we conclude that to take out from food, materials to produce bio ethanol or vegetable oils for biodiesel would not solve the problem of substituting fossil fuels, and would cause hunger.

On the other side, there are large surfaces of arable land, which are not cultivated or which produce plants not suitable for food. In these surfaces, the production of cellulose from trees or bush is possible. On the other side, cellulose containing biomass is a side product of many food crops.

One of the crops which produce large quantities of cellulose is sugar cane, which has an yield of 80 ton per hectar, In one ton of sugar cane there are about 80 kg of sugar, which may be converted to 50 kg of bioethanol. Besides sugar there are 250 kg of cellulose and hemicellulose, which is a much bigger quantity than sugar, which is not converted to liquid fuels. There are also about 80 kg lignin, which may become a useful energy source in the conversion of cellulose in liquid biofuels.

Cellulose, hemicellulose and starch have been studied in the past as possible sources of raw materials for liquid fuels and chemicals.

Wood itself is since thousands of years an energy source. Biomass is used today to produce electricity, but electricity represents only 10% of the consumption of fossil fuels. It is therefore important to find a process to convert cellulose in liquid fuels, suitable for energy supply to transportation and industry, which represent 90% of the consumption of fossil fuels.

The substitution of fossil fuels is also important because of the carbon dioxide which they produce by burning. Although cellulose also produces carbon dioxide by burning, the same quantity of carbon dioxide was taken out of the atmosphere by photosynthesis to produce cellulose.

Although the carbon dioxide content on earth was up to 6000 ppm 100 million years ago, it decreased to 250 ppm in the nineteen century and increased again up to 380 ppm. This sharp increase in the last century is caused by burning fossil fuels and causes dramatic climate changes due to the greenhouse effect.

As a consequence, to convert cellulose into a liquid fuel is since decades a challenge for scientists, because the existing cars and trucks could drive with such a liquid biofuel without major changes in the motor.

The exhausting oil reserves and the political dependence on unstable countries producing oil is also a major problem today.

Electricity is produced today from nuclear or from renewable sources like wind, waves, rivers or photovoltaic, but these sources represent only 20-30% of electricity production. The rest is produced from fossil fuels.

The substitution of liquid fuels by electricity for transports creates a major problem of storage and transportation of electricity, which is technically possible, but far more expensive than the cellulose biofuels.

Because cellulose is renewable, abundant and not producing carbon dioxide by burning if photosynthesis is considered, there has been recent scientific work contained in the Bibliography of this patent application

3. DETAILED DESCRIPTION OF THE INVENTION

It is known that cellulose hydrolyses to glucose in a solvent consisting of N-Alkyl imidazolium chloride (NAIC) mixed with a small quantity of hydrochloric acid. However, under these reaction conditions, glucose dehydrates and produces an undesirable mixture of products.

We made the hydrolysis reaction in a mixture containing NMIC, hydrochloric acid and an alcohol. This alcohol reacted with glucose producing an acetal. In fact, glucose is in equilibrium between 2 forms, the linear form and the cyclic form containing a pyran ring. The pyran ring contains no aldehyde function, but an acetal with the corresponding carbon atom bound to the oxygen of an hydroxyl and the other oxygen atom located in the ring as an ether bond.

We found that the glucose molecules in the linear, open ring form are more reactive, as they contain the aldehyde function.

This aldehyde reacts with the alcohol which we added to the reaction mixture in a large excess. Glucose in this linear form and as an acetal curiously is not able to make a pyran ring again, but makes a furan ring. This glucose acetal in the form of the furan ring is stable under the reaction conditions and does not dehydrate under the reaction conditions used for the hydrolysis of cellulose.

Although the use of an acetal to protect an aldehyde function is well known for those skilled in the art, the application of the acetal to this particular reaction conditions is not at all evident, as we are using an ionic liquid, the pH is under 3, and the conclusion that the hydroxyl groups of glucose are stabilised by the acetal are also not evident.

In a second step we eliminate the water and the alcohol from the reaction mixture and add a small quantity of hydrochloric acid to catalyse the dehydration. After heating at 60-90° C., we produced the acetal of hydroxymethyl furfural.

In order to hydrogenate the acetal of hydroxymethyl furfural, we made 2 extractions, in order to separate very perfectly the NMIC from the acetal of HMF. In fact, even a small quantity of chloride ions can poison the hydrogenation catalyst used in the next step.

We made a first extraction from the NMIC mixture with an alcohol, using as a salting out help a water solution of sodium chloride.

We evaporated the alcohol and mixed with a 5% solution of hydrochloric acid in order to convert all NAI existing in the polar form into NAIC, which is an ionic molecule, therefore easier to separate with organic solvents.

We extracted from the previous mixture the acetal of HMF with a ketone. The cetone extract was washed with water in order to further eliminate chloride ions.

The ketone was evaporated and the concentrate was hydrogenated using an alcohol as a solvent and using as the catalyst a noble metal on alumina on activated carbon.

By distillation we got dimethyl furan.

Example: In a round bottom flask we stirred under reflux at 60° C.:

| | |
|---|---|
| NAIC | 100 g |
| Cellulose | 20 g |
| Hydrochloric acid 37% | 30 g |
| 1-Pentanol | 100 g |
| After one hour, we distilled the water and pentanol. We added to the concentrate: | |
| Hydrochloric acid 37% and heated at 110° C. | 10 g |
| After one hour, we cooled at room temperature and added a 20% sodium chloride solution | 30 g |

We made 3 extractions with 100 g pentanol each extraction. The pentanol extract was evaporated and the concentrate was mixed with:

| | |
|---|---|
| Hydrochloric acid 5% in water | 30 g |
| 3-Pentanone | 80 g |
| After decanting, the pentanone extract was washed 2 times with: | |
| Water | 30 g |

The pentanone extract was evaporated. The concentrate was solved in 1-pentanol. We decided not to hydrogenate the pentanone to avoid its conversion to 3-pentanol, which corresponds to an unnecessary consumption of pentanone in an industrial scale.

The pentanol solution was hydrogenated in a Parr reactor at 150° C. and 50 bar during 3 hours using 6 g of palladium 5% on alumina catalyst.

After distillation we got 10.5 g dimethyl furan as compared to the stoechiometric yield of 12 g.

Information Disclosure Statements

Patents and publications relevant to the patentability of the instant claims, concerning following questions:
dissolution of cellulose in ionic liquids instead of traditional processes using water and organic solvents
hydrolysis and pyrolysis of cellulose
dehydration of fructose in ionic liquids to hydroxylmethyl furfural
hydrogenation in organic solvents of hydroxymethyl furfural to isomers of dimethyl tetrahydrofuran
isomerisation of glucose to fructose 1. Jaroslaw Lewkowski, Synthesis, Chemistry and Applications of 5-Hydroxymethyl-furfural and its derivatives, Arkivoc, 2001, 17-54
2. Claude Moreau, Annie Finiels, Laurent Vanoye, Dehydration of fructose and sucrose into 5-hydroxymethylfurfural in the presence of 1-H-3-methyl imidazolium chloride acting both as solvent and catalyst, journal of Molecular Catalysis A, 2006, 165-169
3. Fred Shafizedh, Saccharification of lignocellulosic materials, Pure and Appl. Chem., vol 55, No 4, pp 705-720, 1983
4. Khavinet Lourvanij and Gregory Rorrer, Reaction rates for the partial dehydration of glucose to organic acids in solid-acid molecular sieving catalyst powders J. Chem. Tech. Biotechnol., 1997, 69, 35-44
5. Yuri Roman Leshkov, Christopher Barrett, Zehn Y. Liu, James A. Dumesic, Production of dimethylfuran for liquid fuels from biomass derived carbohydrates, Nature, Vol 447, 21 Jun. 2007, 982
6. Acid in ionic liquid: an efficient system for hydrolysis of lignincellulose, Changzhi Li et al. Green Chemistry, 17 Dec. 2007
7. Cataklytic conversion of cellulose into Sugar alcohols Atsushi Fukuoka et al. Angewandte Chemie, 2006, 45, 5161-5163
8. Pyranone by pyrolysis of cellulose, Fred Shafizadeh, Pure & Applied Chem, 1983, 55-4, 705-720
9. Dissolution of cellulose with ionic liquids and its application—a minireview, Shengdong Zhu et al, Green Chemistry, 2006, 8, 325-327
10. WO 2008/053284 A1—Liquid biofuels containing dihydroxymethyl furan, Pedro Correia, priority date 9 Mar. 2007.
11. PCT IB 2008 03313, Liquid biofuels containing 2 methyl tetrahydro pyran, Pedro Correia
12. USP application 123566643—Liquid biofuels from cellulose, Pedro Correia
13. Simple chemical transformation of lignocellulosic biomass into furan for fuel and chemicals, J. Am. Chem. Soc. 2009, 131, (5), 1979-1985, Joseph Binder, Ronald Raines
Process for converting cellulose in a liquid biofuel using N-methyl imidazolium chloride

The invention claimed is:

1. A process for obtaining a biofuel consisting of dimethyl furan, by successively dissolving cellulose in a mixture of N-alkyl imidazolium chloride (NAIC), hydrochloric acid 37% and an alcohol, hydrolysing cellulose into the acetal of glucose, evaporating the alcohol and water, dehydrating the glucose acetal to the acetal of hydroxymethyl furfural, adding to the reaction mixture an water solution of sodium chloride, extracting with an alcohol, concentrating the alcohol extract by distillation, mixing the alcohol concentrate with a ketone and a diluted hydrochloric acid solution in order to convert residues of NAI to the corresponding chloride (NAIC), extracting from the ketone phase residues of NAIC by washing several times with water, evaporating the ketone, mixing the concentrate with an alcohol, hydrogenating the almost chloride free alcohol concentrate and isolating the dimethyl furan by distillation.

2. The process of claim 1 where the reaction mixture for hydrolysing cellulose is a mixture containing 20-80% of an ionic liquid composed of N-alkyl imidazolium chloride with the alkyl group with 1 to 10 carbon atoms, containing also 2-15% of hydrochloric acid 37%, and containing an alcohol, which may contain carbon atoms C1-C6 in a quantity that makes the sum of the components of the reaction mixture 100%.

3. The process of claim 1 where the temperature of the hydrolysis reaction is 50-120° C. and the temperature of the dehydration reaction is 60-100° C.

4. The process of claim 1 where the first extraction is made with the same alcohol used for acetal formation, or is another alcohol, with a number of carbon atoms C1-C6, and using a 20% sodium chloride solution mixed to the NAIC phase in a quantity which may vary between 10 and 50% of the NAIC phase.

5. The process of claim 1 where the second extraction is made with a ketone with carbon atoms C3-C7, the concentration of hydrochloric acid may vary from 1-10%, the quantity of the hydrogen chloride solution as well as the washing water is 5-50% of the ketone.

6. The process of claim 1 where the alcohol used as a solvent in the hydrogenation reaction contains carbon atoms C3 to C7, is almost free from chlorides, is hydrogenated with hydrogen gas at a pressure of 2-100 bar, and a temperature of 50-180° C., using as 2-10% catalyst referring to the weight of the reaction mixture and consisting of 2-5% palladium or 2-5% platin on activated coal or alumina.

7. The process of claim 1 where the solution after hydrogenation is submitted to a distillation to isolate the biofuel consisting of dimethyl furan.

8. The process of claim 1 where the water, sodium chloride, alcohol and the NAIC are almost fully recycled.

* * * * *